United States Patent [19]
Townsend et al.

[11] Patent Number: 5,827,833
[45] Date of Patent: Oct. 27, 1998

[54] TRICIRIBINE AND ANALOGS AS ANTIVIRAL DRUGS

[75] Inventors: Leroy B. Townsend; John C. Drach, both of Ann Arbor, Mich.; Louis S. Kucera, Pfaff Town, N.C.

[73] Assignees: Regents of the University of Michigan, Ann Arbor, Mich.; Wake Forest University, Winston-Salem, N.C.

[21] Appl. No.: 769,366

[22] Filed: Dec. 19, 1996

Related U.S. Application Data

[62] Division of Ser. No. 266,847, Jul. 5, 1994, Pat. No. 5,633,235, which is a continuation of Ser. No. 16,302, Feb. 11, 1993, abandoned, which is a continuation of Ser. No. 687,579, Apr. 19, 1991, abandoned.

[51] Int. Cl.[6] .................................................... A61K 31/70
[52] U.S. Cl. .............................................. 514/49; 514/51
[58] Field of Search .......................................... 514/49, 51

[56] References Cited

U.S. PATENT DOCUMENTS 4,123,524  10/1978  Townsend et al. ..................... 424/180

OTHER PUBLICATIONS

Moore et al., "Inhibition of . . . by Triciribine . . . ", Biochem. Pharm. 38(22): 4037–4044, 1989.
Goodman et al., The Pharmacological Basis of Therapeutics, p. 1242, 1985.
Alberts et al., Molecular Biology of the Cell, pp. 238–239, 1983.

*Primary Examiner*—Kimberly Jordan
*Attorney, Agent, or Firm*—Oblon, Spivak, McClelland, Maier & Neustadt, P.C.

[57] ABSTRACT

Triciribine and analogs are effective antiviral agents.

35 Claims, No Drawings

TRICIRIBINE AND ANALOGS AS ANTIVIRAL DRUGS

This is a Division of application Ser. No. 08/266,847 filed on Jul. 5, 1994, now U.S. Pat. No. 5,633,235, which is a Continuation of application Ser. No. 08/016,302, filed Feb. 11, 1993, abandoned, which is a Continuation of application Ser. No. 07/687,579, filed Apr. 19, 1991, abandoned.

BACKGROUND OF THE INVENTION

1. Field of the Invention

The present invention relates to a method of treating retrovirus infections, such as HIV and also herpesvirus infections such as human cytomegalovirus (HCMV) infections, and diseases caused by such infections, such as AIDS, ARC and related expressions of human immunodeficiency virus (HIV), such as lymphadenopathy, by administering triciribine, A triciribine 5'-monophosphate, the DMF adduct of triciribine, or a pharmaceutically acceptable salt thereof to a patient suffering from HIV infection.

2. Discussion of the Background

Acquired immunodeficiency syndrome (AIDS) and AIDS related complex (ARC) result from infection with human immunodeficiency virus (HIV). The need for an effective treatment of AIDS, ARC and lymphadenopathy is great, due to the continuing increase of HIV infections and consequent opportunistic infections such as HCMV in the population. Current epidemiologic data show that infection with HIV leads to AIDS in over 90% of affected individuals within a ten-year period. Tragically, the number of individuals already infected means that the number of AIDS cases will continue to increase for the foreseeable future.

AZT (zidovudine) has been recommended for the treatment of AIDS and ARC. However, results are less than satisfactory. In particular, AZT therapy is known to cause severe side effects, such as anemia. In addition, there are strains of HIV-1 which are resistant to treatment with AZT.

Thus, there remains a need for an effective treatment of HIV infection and AIDS, ARC, and lymphadenopathy.

Human cytomegalovirus (HCMV) is responsible for many life-threatening infections in immunosuppressed patients such as those receiving organ or tissue transplants, cancer patients, burn patients and those afflicted with AIDS. In addition, intrauterine HCMV infections are second only to Down's syndrome as a known cause of mental retardation. Ganciclovir (DHPG) is the only drug available for treatment of some of those infections including CMV gastrointestinal infections and CMV retinitis. Unfortunately, prolonged therapy with ganciclovir causes serious side effects, such as neutropenia, which limits its use. Recently, ganciclovir-resistant strains of HCMV have been isolated from AIDS patients undergoing ganciclovir treatment.

Thus, there also remains a need for an effective treatment of HCMV infection.

SUMMARY OF THE INVENTION

Accordingly, one object of the present invention is to provide a novel method for the treatment of retrovirus infections.

It is another object of the present invention to provide a method of treating HIV infection.

It is another object of the present invention to provide a method of treating HCMV infection.

It is another object of the present invention to provide a method of treating AIDS.

It is another object of the present invention to provide a novel method for treating ARC.

It is another object of the present invention to provide a novel method for treating lymphadenopathy.

These and other objects, which will become apparent during the following detailed description have been achieved by the inventors' discovery that AIDS, ARC, and lymphadenopathy may be treated by administering an effective amount of triciribine, triciribine 5'-phosphate, the DMF adduct of triciribine, or pharmaceutically acceptable salts thereof, to a patient in need thereof.

DETAILED DESCRIPTION OF THE PREFERRED EMBODIMENTS

Triciribine (TCN), triciribine 5'-phosphate (TCN-P), and the DMF adduct of triciribine (TCN-DMF) are known compounds having the formulae:

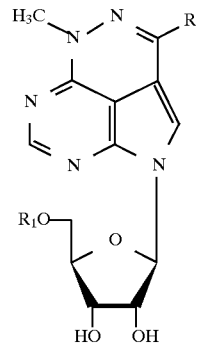

wherein:

| | R | $R_1$ |
|---|---|---|
| TCN | $-NH_2$ | $-H$ |
| TCN-DMF | $-N=CH-N(CH_3)_2$ | $-H$ |
| TCN-P | $-NH_2$ | $-O-\overset{O}{\underset{OH}{\overset{\|}{P}}}-OH$ |

TCN may be synthesized as described in *Tetrahedron Letters*, vol. 49, pp. 4757–4760 (1971), which is incorporated herein by reference. TCN-P may be prepared as described in U.S. Pat. No. 4,123,524, which is incorporated herein by reference. TCN-DMF is described in *INSERM*, vol. 81, pp. 37–82 (1978). Triciribine is currently in phase II clinical trials as an anticancer drug.

Thus, the present invention relates to a method of treating retrovirus infections, such as HIV and HCMV infections, and diseases, such as AIDS, ARC, and lymphadenopathy, said method comprising or consisting of administering an effective amount of TCN, TCN-P, TCN-DMF, or a pharmaceutically acceptable salt thereof to a patient in need thereof.

Although the exact dosage of TCN, TCN-P, TCN-DMF, or a pharmaceutically acceptable salt thereof to be administered will vary according to the size and condition of the patient, a suitable dosage range is 15 to 350 mg/m² of body surface, preferably 15 to 96 mg/m² of body surface, most preferably 25 to 50 mg/m² of body surface.

The TCN, TCN-P, TCN-DMF, or pharmaceutically acceptable salt thereof may be administered according to the present invention by any suitable route, such as intravenously, parenterally, subcutaneously, intramuscularly, or orally. The TCN, TCN-P, TCN-DMF, or pharmaceutically acceptable salt thereof may be administered in any conventional form such as a pharmaceutical composition. Suitable pharmaceutical compositions are those containing, in addition to TCN, TCN-P, TCN-DMF, or pharmaceutically acceptable salt thereof, a pharmaceutically acceptable carrier, such as water, starch, sugar, etc. The composition may also contain flavoring agents and may take the form of a solution, tablet, pill, capsule, etc. The ratio of the weight of TCN, TCN-P, TCN-DMF, or pharmaceutically acceptable salt thereof to the weight of the pharmaceutical composition may, of course, vary but is suitably within 1:1 to 1:5000.

It is to be understood that the present method includes embodiments in which TCN, TCN-P, TCN-DMF, or pharmaceutically acceptable salt thereof is administered to a patient who is also receiving AZT. The present compound(s) and AZT may be administered to the patient in a single composition comprising both the present compounds and AZT. Alternatively, the present compound(s) and AZT may be administered separately. Further, the present method includes embodiments in which AZT is administered, without TCN, TCN-P, TCN-DMF, or a pharmaceutically acceptable salt thereof, for a suitable time period of hours, days, or weeks, and the AZT therapy is either preceded or followed by administration of TCN, TCN-P, TCN-DMF, or a pharmaceutically acceptable salt, either with or without AZT.

For purposes of the present invention, the term pharmaceutically acceptable salt thereof refers to any salt of TCN, TCN-P, or TCN-DMF which is pharmaceutically acceptable and does not greatly reduce or inhibit the activity of TCN, TCN-P, or TCN-DMF. Suitable examples for TCN and TCN-DMF include acid addition salts, with an organic or inorganic acid such as acetate, tartrate, trifluoroacetate, lactate, maleate, fumarate, citrate, methane sulfonate, sulfate, phosphate, nitrate, or chloride. Suitable examples of salts for TCN-P include those in which one or more of the acidic phosphate hydrogens has been replaced with an ion, such as sodium, potassium, calcium, iron, ammonium, or mono-, di- or tri-lower-alkyl ammonium, in addition to the acid addition salts described above. It is to be further understood that the terms TCN, TCN-P, TCN-DMF, and pharmaceutically acceptable salts thereof include all the hydrated forms of these compounds as well as the anhydrous forms.

The present method has been found to exhibit the following advantages:

1) Like zidovudine, triciribine is active against both clinical and laboratory stains and isolates of HIV-1 and HIV-2 at concentrations which are not overtly cytotoxic in uninfected cells.

2) Triciribine is active against strains of HIV-1 which have become resistant to zidovudine as a consequence of long term use of zidovudine in patients.

3) Triciribine is active against both HIV and HCMV whereas zidovudine is only active against HIV and ganciclovir is only active against HCMV and other herpesviruses.

4) Triciribine acts by a biochemical mechanism totally different from zidovudine and other antivirals active against HIV and HCMV.

5) The cytotoxicity of triciribine is not synergistic with that of zidovudine in clinically useful dose ranges.

Thus, TCN, TCN-P, and TCN-DMF have been found to inhibit HIV-1 induced RT, p24 core antigen, and infectious virus production in a dose dependent manner using acutely infected H9 and chronically infected H9-IIIB and U1 cells. In a microtiter XTT assay, TCN exhibits an $IC_{50}$ of 0.26–0.46 $\mu$M against HIV-$1_{RF}$, HIV-$1_{IIIB}$, and HIV-$1_{MN}$ while TCN-P has an $IC_{50}$ of 0.02–0.03 $\mu$M against these isolates. TCN and TCN-P also are active against a panel of HIV-1 and HIV-2 isolates measured by XTT assay. Activity was also demonstrated in fresh human peripheral blood lymphocytes and macrophages infected with clinical isolates of HIV-1, TCN and TCN-P inhibited HIV in chronically infected cells (U1 and CEM) as measured by a reduction in the number of syncytia formed in microtiter assays. HIV resistant to AZT inhibition did not show cross resistance to TCN or TCN-P. In vitro activity was similarly detected against Rauscher MuLV in an UV-XC plaque reduction assay with an observed $IC_{50}$ of 0.12 $\mu$M for TCN and 0.07 $\mu$M for TCN-P. RT inhibition assays utilizing TCN, TCN-monophosphate, and TCN-triphosphate have demonstrated that the compounds do not act via inhibition of this enzyme.

Of course, the present invention may be practiced in various embodiments which exclude any step or element not expressly described herein.

Other features of the invention will become apparent in the course of the following descriptions of exemplary embodiments which are given for illustration of the invention and are not intended to be limiting thereof.

EXAMPLES

A. Methods

1. Propagation of Cells a. Cells for Cytotoxicity Assays and Propagation of Human Cytomegalovirus (HCMV)

The routine growth and passage of KB cells—a human epidermoid neoplastic cell line—was performed in monolayer cultures using minimal essential medium (MEM) with either Hanks salts [MEM(H)] or Earle salts [MEM(E)] supplemented with 10% calf serum or 5 to 10% fetal bovine serum. The sodium bicarbonate concentration was varied to meet the buffering capacity required. Cultures of diploid human foreskin fibroblasts (HFF) were grown in medium consisting of MEM(E) with 10% fetal bovine serum.

Cells were passaged at 1:2 to 1:10 dilutions according to conventional procedures by using 0.05% trypsin plus 0.02% EDTA in a HEPES buffered salt solution. HFF cells were passaged only at 1:2 dilutions.

b. Cells for Cytotoxicity Assays and Propagation of Human Immunodeficiency Virus (HIV)

The cells used for routine screening were the MT-2 (Harada et al., Science 229:563–566, 1985) and CEM (Nara and Fischinger, Nature 332:469–470, 1988) cell lines. Cells were grown in RPMI 1640 medium supplemented with 20% (v/v) fetal calf serum (H9 cells) or 10% fetal calf serum (MT-2 and CEM cells). The medium also contained 100 units/ml penicillin, 100 mcg/ml streptomycin, and 25 mM HEPES buffer. The medium used for dilution of drugs and maintenance of cultures during the assay was the same as the above with 10% serum. Cultures were maintained in disposable tissue culture labware at 37° C. in a humidified atmosphere of 5% $CO_2$ in air.

2. Propagation of Viruses a. HIV

The HTLV-IIIB and other strains of HIV-I were propagated in the human T-lymphocyte cell line, H9 (Popovic, M. et al., Science 224:497–500, 1984). The virus inoculum consisted of supernatant fluids from H9-IIIB producer cultures.

b. HCMV

Stock HCMV was prepared by infecting HFF cells at a multiplicity of infection (m.o.i.) of <0.01 plaque-forming units (p.f.u.) per cell. Cell growth medium was changed every four days until cytopathology was evident in all cells (approximately 21 days). Supernatant fluids were retained as the virus stock. Four days later the remaining cells were disrupted by three cycles of freeze-thawing and the cells plus medium held as an additional source of virus. Storage was in liquid nitrogen.

HCMV was titered in 24-well cluster dishes which were planted to contain $5\times10^4$ HFF cells/well, grown as described above. When the cells were 70 to 80% confluent, 0.2 ml of the virus suspension was added per well and adsorbed as described above. At least three one-logarithm dilutions of each preparation were used. Following virus adsorption, the cell sheets were overlaid with 0.5% methocel (4000 CPS) in maintenance medium [MEM(E) with 1.1 gm/liter $NaHCO_3$, 100 units/ml penicillin G, 100 µg/ml streptomycin, and 5% fetal bovine serum]. The cultures were incubated in a humidified atmosphere of 4% $CO_2$-96% air. Viral foci were visible 5 to 7 days after infection using at least 10-fold magnification. Cells were fixed and stained by a 10-minute exposure to a 0.1% solution of crystal violet in 20% methanol 7 to 12 days after infection. Microscopic foci were enumerated at 20 to 30 fold magnification.

3. Assays for Antiviral Activity a. HCMV

The effect of compounds on the replication of HCMV has been measured using both a plaque (focus) reduction assay and a titer (yield) reduction assay. For the former, HFF cells in 24-well cluster dishes were infected with approximately 100 p.f.u. of HCMV per $cm^2$ cell sheet using the procedures detailed above. Compounds dissolved in growth medium were added in three to six selected concentrations to triplicate wells following virus adsorption. Following incubation at 37° C. for 7 to 10 days, cell sheets were fixed, stained and microscopic foci were enumerated as described above. Drug effects were calculated as a percentage of reduction in number of foci in the presence of each drug concentration compared to the number observed in the absence of drug. DHPG (ganciclovir) has been used as a positive control in all experiments.

For titer reduction assays, HFF cells were planted as described above in 24-well cluster dishes or in 25 $cm^2$ flasks. When monolayers were approximately 70% confluent, HCMV was added at a m.o.i. of 0.5 p.f.u. per cell and adsorbed as detailed above. Compounds dissolved in growth medium were added in one or one-half logarithm dilutions and incubation continued at 37° C. After 7 to 10 days of incubation, culture dishes or flasks were frozen at −76° C. For titer determination, cells were thawed and then subjected to two more cycles of freezing and thawing at 37° C. Serial, one-logarithm dilutions of the final suspension were prepared and inoculated onto new cultures of HFF cells. Titer determination was as detailed above.

b. HIV by Syncytial Assay

To measure specific inhibition of HIV-1 syncytium formation, serial twofold dilutions of test compound at concentrations below the $IC_{30}$ for cell growth inhibition were used. CEM-SS cells were seeded at 10,000 cells per well into 96-cell plates precoated with poly L-lysine. The cell monolayers were infected with about 50 plaque forming units of HIV-1. After 1 hr for virus attachment, the cell monolayers were overlaid with growth medium with or without added test compound. After 3 days incubation at 37° C. in a $CO_2$ incubator, the cell monolayers received a second overlay of growth medium with or without added test compound and incubation at 37° C. continued for a total of 5 days. HIV-1 plaques were counted, the counts entered into a computer and a $IC_{50}$ for HIV-1 plaque formation was determined. Each experiment was replicated at least once.

c. HIV by Colorimetric (XTT) Assay

1) Drug Dilution and Addition to Plates

Drugs were dissolved in DMSO at 40 mg/ml or in sterile deionized water at 2 mg/ml, unless otherwise specified. Drug dilutions were made in medium. Drugs in DMSO were initially diluted to 1/200; drugs in water diluted to 1/10. Subsequent dilutions were made in log or 0.5 log series. Each dilution was added to plates in the amount of 100 µl/well. Drugs were tested in triplicate wells per dilution with infection cells, and in duplicate wells per dilution with uninfected cells for evaluation of cytotoxicity. After addition of cells to plates (see following section), the highest drug concentration was 100 µg/ml. The highest DMSO concentration was 0.25%.

2) Infection and Distribution of Cells to Microtiter Plates

A viable cell count (trypan blue) was performed on the cells to be used.

The desired total number of polybrene treated cells was placed in a 50 ml conical centrifuge tube (sterile, disposable), and virus was added to give a MOI of 0.03 $TCID_{50}$/cell on MT-2 cells and approximately 0.12 $TCID_{50}$/cell on CEM cells. Fresh medium was added to adjust the cell density to $1\times10^5$ cells/ml, and the virus-cell suspension is incubated at 37° C. for 1–2 hours until ready for plating.

Uninfected cells were prepared in the same manner but without addition of virus. Cell pellets were collected by low speed centrifugation and supernates were discarded. Infected and uninfected cells were resuspended in appropriate volume of medium and added to plates in the amount of 100 µl/well to give a starting cell number of $1\times10^4$ cells/well. Plates were incubated for 7 days in a humidified atmosphere of 5% $CO_2$ in air.

3) Quantitation of Viral Cytopathic Effect (CPE) and Drug Activity

On day 7 post-infection, the viable cells were measured with a tetrazolium salt, XTT, added to the test plates. A solution was used to dissolve the XTT formazan produced. The optical density value is a function of the amount of formazan produced which is proportional to the number of viable cells. Plates were read at a wavelength of 570 nm on a $V_{max}$ plate reader (Molecular Devices). The percent inhibition or CPE per drug concentration was measured as test over control and expressed in percent.

4) Cytotoxicity Assays a. [$^3$H] Thymidine Incorporation

Test compounds solubilized in DMSO were serially diluted in RPMI 1640 medium supplemented with 20% fetal bovine serum (growth medium). Six serial twofold dilutions spanning a concentration range of 100 to 3 µm were tested in triplicate for inhibition of [$^3$H]thymidine uptake into cellular DNA. CEM-SS cells were seeded in 96 well plates (10,000 cells per well) in growth medium containing various concentrations of test compound and incubated at 37° C. in a $CO_2$ incubator. After 36 hours incubation the cells were pulse-labeled for 4 hours at 37° C. with 1 µCi $^3$H-TdR uptake into cellular DNA. Controls consisted of CEM-SS cells not treated with drug and pulse-labeled for 4 hours with [$^3$H]thymidine (positive control) or harvested immediately after addition of [$^3$H]thymidine (negative control). The harvested samples were counted by scintillation spectrometry to obtain a mean±one S.D. for each set of triplicate wells. The data were entered into a computer and used to determine a $IC_{50}$ for cell cytotoxicity. Each experiment was replicated at least once.

b. Visual Scoring

Cytotoxicity produced in HFF and BSC-1 cells has been estimated by visual scoring of cells not affected by virus infection in the HCMV plaque reduction assays. Cytopathology was estimated at 35- and 60-fold magnification and scored on a zero to four plus basis. Wells were scored on the day of staining.

C. Cell Growth Rates

Population doubling times and cell viability were measured in uninfected HFF and/or KB cells. Cells were planted in replicate 6-well plastic tissue culture dishes or in 25 cm² flasks as described above. Following an incubation period during which cells attached to the substrate, medium was decanted, the cell sheet rinsed once with HBS, and fresh medium added. The medium consisted of MEM(E) with 1.1 gm $NaHCO_3$/liter and 10% fetal bovine or calf serum plus appropriate log or half-log concentrations of drug. After additional periods of incubation from 1 to 72 hr at 37° C., cells were harvested by means of 0.05% trypsin plus 0.02% EDTA in a HEPES-buffered salt solution. Cells were enumerated using either a Coulter counter or a hemocytometer and viability determined using trypan blue dye exclusion d. Plating Efficiency A plating efficiency assay was used to confirm and extend the results described above. KB cells were suspended in growth medium and an aliquot containing 500–600 cells was added to a 140×25 mm petri dish. Growth medium (40 ml) containing selected concentrations of test compounds was added and the cultures incubated in a humidified atmosphere of 4% $CO_2$-96% air, 37° C. for 14 days. Medium then was decanted and colonies fixed with methanol an stained with 0.1% crystal violet in 20% methanol. Macroscopic colonies >1 mm in diameter were enumerated. Drug effects were calculated as a percentage of reduction in the number of colonies formed in the presence of each drug concentration compared to the number of colonies formed in the absence of drugs. Dose-response curves were generated and $I_{50}$ concentrations for inhibition of plating/colony formation were calculated.

e. XTT Colorimetric Assay

The assay was performed as described above for the determination of HIV by calorimetric XTT assay except that CEM and MT2 cells were not infected with HIV.

5. Data Analysis

Dose-response relationships were used to compare drug effects. These were constructed by linearly regressing the percent inhibition of parameters derived in the preceding sections against log drug concentrations. The 50% inhibitory ($I_{50}$) concentrations were calculated from the regression lines.

B. Results

Test results are set forth in the following Tables I, II and III.

a. Activity Against HIV, HCMV and Cytotoxicity

Triciribine (TCN), triciribine-5'-monophosphate (TCN-P), and the dimethylformamide adduct of TCN were evaluated for activity against HIV and HCMV. All three compounds were active against both viruses. Fifty percent inhibitory concentrations for HIV-1 were in the range of 0.01 to 0.26 $\mu$M (Table 1). Comparable cytotoxicity ranges for these compounds were from 19 to 45 $\mu$M giving a differential selectivity against HIV from 79-fold (TCN adduct) to 2250-fold (TCN). In contrast, even though the anti-HIV potency of the known anti-HIV drug zidovudine (AZT) was greater than that of the TCN analogs, its cytotoxicity (measured by [³H]thymidine incorporation) also was greater. This resulted in a lower differential selectivity against the virus for AZT (Table 1).

TCN, TCN-P and TCN adduct also were active against HCMV, an opportunistic infection in many AIDS patients. The compounds were not as active against this virus as they were against HIV. Nonetheless, any activity against HCMV in AIDS patients harboring HCMV is beneficial. In contrast, AZT was inactive against HCMV.

b. Verification of Activity Against HIV and Activity Against Clinical Isolates

The activity of TCN and TCN-P illustrated in Table 1 was confirmed and extended by means of other assay methods. Table II shows that the activity of TCN and TCN-P was virtually the same regardless of whether measurement of HIV was by syncytial assay, infectious virus assay, reverse transcriptase activity determination, or by p24 core antigen quantitation.

The activity of TCN and TCN-P against HIV was broadened to include activity against clinical isolates of HIV-1 and HIV-2. Table II illustrates that both compounds were active against many clinical isolates of HIV-1 as well as one isolate of HIV-2. The compounds also were active (but less potent) against Rauscher murine leukemia virus.

The activity of TCN and TCN-P also was evaluated in persistently infected monocyte/macrophages and T-cells. Both compounds were active in reducing HIV production when measured by reverse transcriptase assay, appearance of p24 core antigen, or infectious virus production (Table II). In contrast, other fraudulent nucleosides [such as zidovudine (AZT) and dideoxycytidine (ddC)] are not active against HIV in these assays.

c. Broadened Cytotoxicity Testing

The cytotoxicity of TCN and TCN-P was examined more extensively in other human cell lines using other methods. The results presented in Table II verified the level of cytotoxicity observed by measurement of the effect of the compounds of [³H]thymidine incorporation (Table 1). Assays included calorimetric measurement of enzyme activity (XTT assay) in transformed T cells (CEM, MT2 cells), visual inspection of human diploid foreskin fibroblasts, and growth and plating efficiency of human KB cancer cells. Results were consistent among the cells and assays and showed that TCN-P was more cytotoxic than TCN in vitro. The results also confirmed that the cytotoxic effects occurred at concentrations approximately 1000-fold above concentrations needed to inhibit HIV replication.

d. Activity in HIV Resistant to the Activity of AZT

The activity of TCN and TCN-P was determined in two pairs of clinical isolates obtained from patients before and after they had become refractory to treatment with AZT. Table III shows that despite the fact that the activity of AZT declined by 1000 to over 7000-fold in HIV isolated from patients after AZT therapy, the viruses remained fully sensitive to inhibition by TCN and TCN-P.

TABLE I

Antiviral Activity and Cytotoxicity in Human Cells of Triciribine (TCN) Analogs and Zidovudine (AZT).

| | 50% Inhibitory Concentration ($\mu$M) | | |
| --- | --- | --- | --- |
| Assay and Compound | Antiviral Activity | Cytotoxicity | Differential Selectivity |
| Antiviral Activity: HIV[a] | | | |
| Triciribine (TCN) | 0.02 | 45 | 2250 |
| Triciribine 5'-monophosphate (TCN-P) | 0.01 | 19 | 1900 |
| Triciribine dimethylformamide | 0.026 | 20.5 | 79 |

TABLE I-continued

Antiviral Activity and Cytotoxicity in
Human Cells of Triciribine (TCN) Analogs and Zidovudine (AZT).

| | 50% Inhibitory Concentration (μM) | | |
|---|---|---|---|
| Assay and Compound | Antiviral Activity | Cytotoxicity | Differential Selectivity |
| adduct (TCN-DMF) | | | |
| Zidovudine (AZT) | 0.0027 | 5 | 1852 |
| Antiviral Activity: HCMV[b] | | | |
| Triciribine (TCN) | 2 | 100 | 50 |
| Triciribine 5'-monophosphate (TCN-P) | 0.7 | 19 | 27 |
| Triciribine dimethylformamide adduct (TCN-DMF) | 3.4 | 50 | 15 |

[a]HIV determined by syncytial assay in CEM-SS cells, cytotoxicity assay by uptake of [$^3$H]thymidine in uninfected CEM-SS cells.
[b]HCMV determined by plaque assay in HFF cells, cytotoxicity assay by visual inspection of uninfected HFF cells.

TABLE II

Antiviral Activity and Cytotoxicity in Human Cells
of Triciribine (TCN) and Triciribine-5'-monophosphate (TCN-P)

| Virus or | 50% Inhibitory Concentration (μM) | |
|---|---|---|
| Assay and Cell Line | TCN | TCN-P |
| Antiviral Activity: HIV | | |
| Acute Infection with HIV-1$_{IIIB}$ | | |
| Syncytical assay | 0.03 | 0.01 |
| Infectious virus assay | 0.01 | 0.02 |
| Reverse transcriptase assay | 0.03 | 0.03 |
| p24 Core antigen assay | 0.03 | 0.02 |
| Acute Infection XTT assay | | |
| HIV-1$_{IIIB}$ | 0.46 | 0.02 |
| HIV-1$_{TPI}$ | 0.46 | 0.07 |
| HIV-1$_{TPI}$ | 0.51 | — |
| HIV-1$_{RF}$ | 0.46 | 0.03 |
| HIV-1$_{RF}$ | 0.04 | — |
| HIV-1$_{KELL\ 50}$ | >0.29[a] | — |
| HIV-1$_{KELL\ 40}$ | 0.46 | >2.8 |
| HIV-1$_{MM}$ | 0.26 | 0.02 |
| HIV-1$_{G\ 5}$ | 0.46 | 0.15 |
| HIV-1$_{SKI}$ | >2.9 | 0.19 |
| HIV-1$_{214}$ | 0.9 | 0.08 |
| HIV-1$_{ED}$ | 0.05 | >2.8 |
| HIV-1$_{C}$ | 0.04 | 0.06 |
| HIV-1$_{205}$ | >2.9 | >2.8 |
| HIV-1$_{PM16}$ | <0.46 | 0.11 |
| HIV-1$_{PM16}$ | >2.9 | — |
| HIV-1$_{LAV}$ | <0.46 | 0.07 |
| HIV-1$_{LAV}$ | 0.13 | — |
| HIV-1$_{CPI}$ | >2.9 | — |
| HIV-1$_{MCK}$ | 0.04 | — |
| HIV-2$_{ROD}$ | 0.03 | 0.02 |
| HIV-2$_{MS}$ | >2.3 | — |
| Plaque Reduction | | |
| Rauscher murine leukemia virus | 0.12 | 0.07 |
| Persistent Infection (monocyte/macrophase)[b] | | |
| Reverse transcriptase | 0.1 | 0.08 |
| p24 core antigen | 0.5 | 0.2 |
| Infectious virus | 1.2 | 0.3 |
| Persistent Infection (H9III$_B$ T-cells)[c] | | |

TABLE II-continued

Antiviral Activity and Cytotoxicity in Human Cells
of Triciribine (TCN) and Triciribine-5'-monophosphate (TCN-P)

| Virus or | 50% Inhibitory Concentration (μM) | |
|---|---|---|
| Assay and Cell Line | TCN | TCN-P |
| Reverse transcriptase | 0.03 | 0.05 |
| p24 core antigen | 0.02 | 0.03 |
| Infectious virus | 0.02 | 0.02 |
| Cytotoxicity [$^3$H]dThd Incorporation | | |
| (CEM-SS cells) | 43 | 19 |
| XTT Assay (CEM cells) | 132 | >2.4 |
| XTT Assay (MT2 cells) | 12 | 1.0 |
| Visual (foreskin fibroblasts) | 100 | 6 |
| Cell Growth (KB cells) | — | 10 |
| Plating efficiency (KB cells) | >10 | 3.5 |

[a]Highest concentration tested.
[b]Determined three days post infection.
[c]Determined 12 days post infection.

TABLE III

Comparison of the Activity of Triciribine (TCN),
Triciribine-5'-monophosphate (TCN-P), and Zidovudine (AZT)
in Human Immunodeficiency Virus Sensitive and Resistant to AZT

| Virus and | Syncytial Assay 50% Inhibitory concentration (μM) | | |
|---|---|---|---|
| Strain | AZT | TCN | TCN-P |
| HIV-1$_{IIIB}$ | 0.002 | 0.03 | 0.01 |
| HIV-1$_{G-762}$ (pre AZT therapy)[a] | 0.0002 | 0.028 | 0.035 |
| HIV-1$_{G-691}$ (post AZT therapy)[b] | 0.21 | 0.040 | 0.043 |
| HIV-1$_{H-1112}$ (pre AZT therapy) | <0.001 | 0.050 | 0.16 |
| HIV-1$_{G-910}$ (post AZT therapy) | 7.2 | 0.073 | 0.058 |

[a]Clinical isolate which was sensitive to AZT before therapy
[b]Clinical isolate which become resistant to AZT during chronic therapy.

What is claimed as new and desired to be secured by Letters Patent of the United States is:

1. A method for treating HIV infection, comprising administering an effective amount of triciribine, triciribine DMF adduct, triciribine 5'-phosphate, or a pharmaceutically acceptable salt thereof to a patient in need thereof.

2. The method of claim 1, further comprising administering an effective amount of AZT to said patient.

3. The method of claim 1, wherein triciribine is administered to said patient.

4. The method of claim 3, wherein triciribine is administered to said patient in an amount of 15 to 350 mg/m$^2$ of body surface.

5. The method of claim 3, wherein triciribine is administered to said patient in an amount of 25 to 50 mg/m$^2$ of body surface.

6. The method of claim 3, wherein triciribine is administered to said patient orally.

7. The method of claim 3, wherein triciribine is administered to said patient intravenously.

8. The method of claim 3, wherein triciribine is administered to said patient parenterally.

9. The method of claim 3, wherein triciribine is administered to said patient subcutaneously.

10. The method of claim 3, wherein triciribine is administered to said patient intramuscularly.

11. The method of claim 3, wherein triciribine is administered to said patient in a form selected from the group consisting of solutions, tablets, pills, and capsules.

12. The method of claim 3, wherein a salt of triciribine is administered to said patient.

13. The method of claim 12, wherein said salt of triciribine contains an anion selected from the group consisting of acetate, tartrate, triflouroacetate, lactate, maleate, fumarate, citrate, methane sulfonate, sulfate, phosphate, nitrate, and chloride.

14. The method of claim 1, wherein triciribine DMF adduct is administered to said patient.

15. The method of claim 14, wherein triciribine DMF adduct is administered to said patient in an amount of 15 to 350 mg/m$^2$ of body surface.

16. The method of claim 14, wherein triciribine DMF adduct is administered to said patient in an amount of 25 to 50 mg/ml$^2$ of body surface.

17. The method of claim 14, wherein triciribine DMF adduct is administered to said patient orally.

18. The method of claim 14, wherein triciribine DMF adduct is administered to said patient intravenously.

19. The method of claim 14, wherein triciribine DMF adduct is administered to said patient parenterally.

20. The method of claim 14, wherein triciribine DMF adduct is administered to said patient subcutaneously.

21. The method of claim 14, wherein triciribine DMF adduct is administered to said patient intramuscularly.

22. The method of claim 14, wherein triciribine DMF adduct is administered to said patient in a form selected from the group consisting of solutions, tablets, pills, and capsules.

23. The method of claim 14, wherein a salt of triciribine DMF adduct is administered to said patient.

24. The method of claim 23, wherein said salt of triciribine DMF adduct contains an anion selected from the group consisting of acetate, tartrate, triflouroacetate, lactate, maleate, fumarate, citrate, methane sulfonate, sulfate, phosphate, nitrate, and chloride.

25. The method of claim 1, wherein triciribine 5'-phosphate is administered to said patient.

26. The method of claim 25, wherein triciribine 5'-phosphate is administered to said patient in an amount of 15 to 350 mg/m$^2$ of body surface.

27. The method of claim 25, wherein triciribine 5'-phosphate is administered to said patient in an amount of 25 to 50 mg/m$^2$ of body surface.

28. The method of claim 25, wherein triciribine 5'-phosphate is administered to said patient orally.

29. The method of claim 25, wherein triciribine 5'-phosphate is administered to said patient intravenously.

30. The method of claim 25, wherein triciribine 5'-phosphate is administered to said patient parenterally.

31. The method of claim 25, wherein triciribine 5'-phosphate is administered to said patient subcutaneously.

32. The method of claim 25, wherein triciribine 5'-phosphate is administered to said patient intramuscularly.

33. The method of claim 25, wherein triciribine 5'-phosphate is administered to said patient in a form selected from the group consisting of solutions, tablets, pills, and capsules.

34. The method of claim 25, wherein a salt of triciribine 5'-phosphate is administered to said patient.

35. The method of claim 34, wherein said salt of triciribine 5'-phosphate contains an ion selected from the group consisting of sodium, potassium, calcium, iron, ammonium, di-lower-alkyl ammonium, tri-lower-alkyl ammonium, acetate, tartrate, triflouroacetate, lactate, maleate, fumarate, citrate, methane sulfonate, sulfate, phosphate, nitrate, and chloride.

* * * * *

UNITED STATES PATENT AND TRADEMARK OFFICE
CERTIFICATE OF CORRECTION

PATENT NO. : 5,827,833
DATED : October 27, 1998
INVENTOR(S) : Townsend et al

It is certified that error appears in the above-identified patent and that said Letters Patent is hereby corrected as shown below:

ON THE TITLE PAGE

After the Title, please insert:

--This invention was made with government support under Contract No. 72641 and Cooperative Agreement No. 25739 awarded by the National Institute of Allergy and Infectious Diseases of the National Institutes of Health. The government has certain rights in the invention.--

Signed and Sealed this

Tenth Day of August, 1999

Attest:

Q. TODD DICKINSON

Attesting Officer

Acting Commissioner of Patents and Trademarks

UNITED STATES PATENT AND TRADEMARK OFFICE
CERTIFICATE OF CORRECTION

PATENT NO. : 5,827,833
DATED : October 27, 1998
INVENTOR(S) : Leroy B. TOWNSEND

It is certified that error appears in the above-identified patent and that said Letters Patent is hereby corrected as shown below:

Column 7, line 28, delete "an" and insert --and--.

Signed and Sealed this

Fourth Day of July, 2000

Attest:

Q. TODD DICKINSON

*Attesting Officer*      *Director of Patents and Trademarks*